(12) United States Patent
Luk

(10) Patent No.: US 7,544,943 B2
(45) Date of Patent: Jun. 9, 2009

(54) METHOD AND SYSTEM FOR REMOTE EXHAUST EMISSION MEASUREMENT

(75) Inventor: Wai Ming Luk, Kowloon (HK)

(73) Assignee: Mutual Sky Technology Limited, Kowloon (HK)

( * ) Notice: Subject to any disclaimer, the term of this patent is extended or adjusted under 35 U.S.C. 154(b) by 0 days.

(21) Appl. No.: 11/651,587

(22) Filed: Jan. 10, 2007

(65) Prior Publication Data

US 2007/0164220 A1 Jul. 19, 2007

Related U.S. Application Data

(60) Provisional application No. 60/759,588, filed on Jan. 18, 2006.

(51) Int. Cl.
*G01N 21/00* (2006.01)

(52) U.S. Cl. .................................................. 250/338.5

(58) Field of Classification Search .... 250/338.1–338.5
See application file for complete search history.

(56) References Cited

U.S. PATENT DOCUMENTS

| | | | | |
|---|---|---|---|---|
| 3,498,312 | A * | 3/1970 | Geiszler | 137/102 |
| 4,479,914 | A * | 10/1984 | Baumrucker | 264/45.5 |
| 4,489,239 | A * | 12/1984 | Grant et al. | 250/339.03 |
| 4,591,721 | A * | 5/1986 | Wong | 250/373 |
| 4,678,914 | A | 7/1987 | Melrose et al. | |
| 4,924,095 | A | 5/1990 | Swanson, Jr. | |
| 5,171,455 | A * | 12/1992 | Wang et al. | 210/744 |
| 5,210,702 | A | 5/1993 | Bishop et al. | |
| 5,319,199 | A | 6/1994 | Stedman et al. | |
| 5,401,967 | A | 3/1995 | Stedman et al. | |
| 5,498,872 | A | 3/1996 | Stedmam et al. | |
| 5,583,765 | A * | 12/1996 | Kleehammer | 701/1 |
| 5,591,975 | A | 1/1997 | Jack et al. | |
| 5,726,450 | A * | 3/1998 | Peterson et al. | 250/338.5 |
| 5,797,682 | A | 8/1998 | Kert et al. | |
| 5,831,267 | A | 11/1998 | Jack et al. | |
| 6,078,048 | A | 6/2000 | Stevens et al. | |
| 6,455,851 | B1 * | 9/2002 | Lord et al. | 250/338.5 |

(Continued)

FOREIGN PATENT DOCUMENTS

WO WO 00/42415 7/2000

(Continued)

OTHER PUBLICATIONS

International Search Report of Counterpart PCT patent application.

(Continued)

*Primary Examiner*—David P. Porta
*Assistant Examiner*—Kiho Kim

(57) ABSTRACT

A remote vehicle emissions measurement system including a radiation source, an adaptable radiation detection unit and a processing unit, characterized in that the radiation source includes an infrared source, an ultraviolet source or a combination thereof; the radiation detection unit includes one or more detachable and expandable detecting elements for receiving the set of predetermined wavelength bands and producing a plurality of corresponding responses concurrently at any one time instant; and the processing unit includes one or more specific software and hardware for calculating the concentrations of various gas components thereof, the relative ratio of one gas component to the others, or the absolute emission values of each of the gas components thereof in an accurate and practicable manner.

19 Claims, 5 Drawing Sheets

U.S. PATENT DOCUMENTS

| | | | |
|---|---|---|---|
| 6,723,989 B1 * | 4/2004 | Didomenico et al. | 250/339.05 |
| 6,903,329 B2 * | 6/2005 | Gentala | 250/238 |
| 7,141,793 B2 * | 11/2006 | Johnson et al. | 250/338.5 |
| 7,164,132 B2 * | 1/2007 | Didomenico et al. | 250/338.5 |
| 7,253,903 B2 * | 8/2007 | Sachse et al. | 356/437 |
| 2003/0040854 A1 | 2/2003 | Rendahl et al. | |
| 2004/0104345 A1 * | 6/2004 | Kansakoski et al. | 250/338.5 |
| 2005/0076088 A1 * | 4/2005 | Kee et al. | 709/206 |
| 2005/0197794 A1 | 9/2005 | Full | |

FOREIGN PATENT DOCUMENTS

| | | |
|---|---|---|
| WO | WO2005/077001 | 8/2005 |

OTHER PUBLICATIONS

Written Opinion of Counterpart PCT patent application.

Search Report of Counterpart Hong Kong short-term patent application.

* cited by examiner

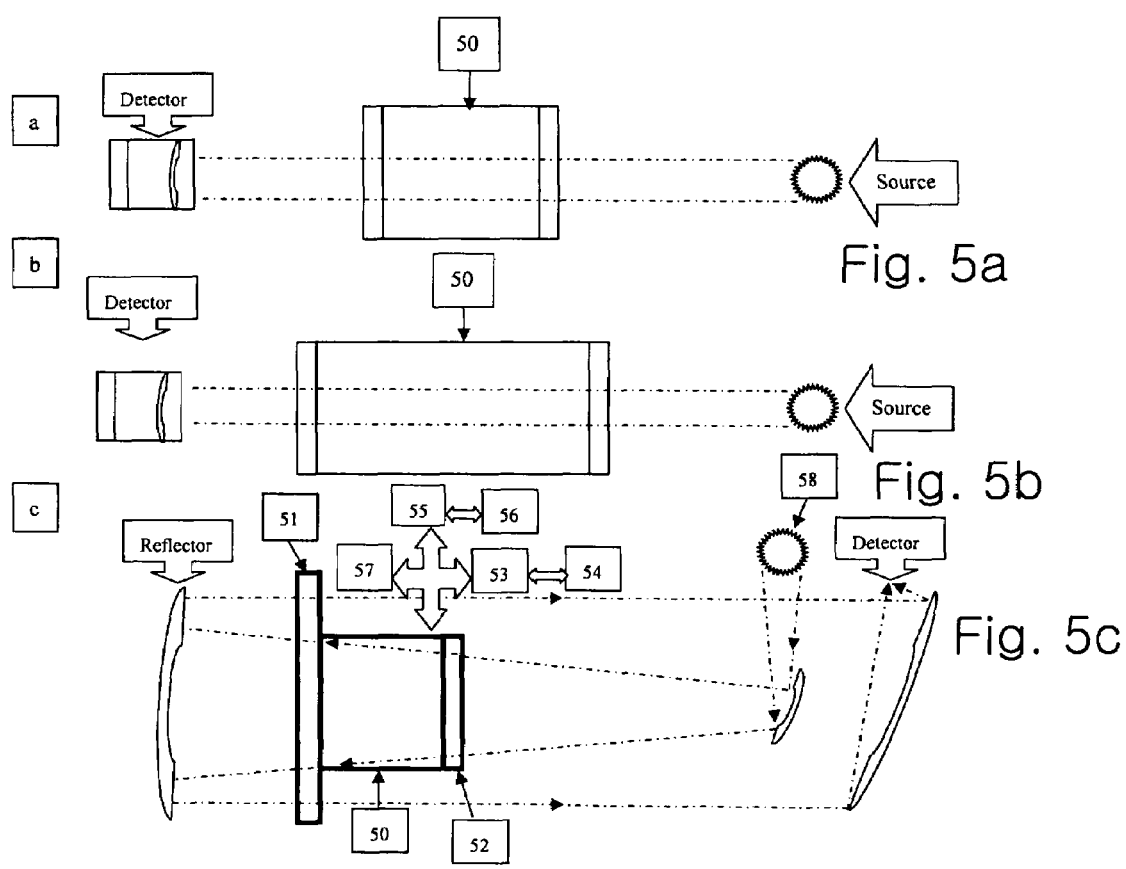

METHOD AND SYSTEM FOR REMOTE EXHAUST EMISSION MEASUREMENT

CROSS-REFERENCE TO RELATED APPLICATIONS

The present invention claims priority to U.S. Provisional Patent Application Ser. No. 60/759,588 as filed in Jan. 18, 2006, which is in whole incorporated herein by reference.

FIELD OF THE INVENTION

The present invention relates to remote exhaust emissions analysis, more particularly to methods and systems for remote exhaust emissions measuring.

BACKGROUND OF THE INVENTION

It is well known that the exhaust emissions from a vehicle may be detected and characterized by a remote sensing system, wherein a rotating device, such as a reflecting wheel or a movable filter is incorporated for allowing one or more detectors to receive a beam with different wavelength bands passing through the emission plume, whereby various gas components of the plume can be analyzed and monitored.

Such a remote sensing system is disclosed in U.S. Pat. No. 5,210,702, in which a collimated beam emitted from a radiation source passes through the exhaust plume of a vehicle and is reflected from an adjustable mirror onto a reflecting wheel therein. The beam is then reflected therefrom to the focusing mirrors thereof and in turn directed at a plurality of detectors through the respective filters.

Another gas analysis device is disclosed in WO 00/42415, wherein a beam emitted from a radiation source passes through an emission plume of a vehicle.

The beam may optionally be focused on a detector by a lens. The light beam also passes through a set of moveable filters before it impinges on the detector. Alternatively, the beam may optionally be focused on a detector by a lens via reflection off of one or more of a moveable set of reflective filters, which may reflect only the wavelengths of specific detection bands of radiation for detection of different components of the vehicle emission plume.

Further, the moveable set of filters may comprise a rotating filter wheel with filters mounted on the wheel. Such filter wheel is mounted for rotation about its axis. Various filters are mounted on the filter wheel; thereby the filter wheel may be rotated on its axis to align different filters with a single detector at different times. Each filter permits only a specific detection band of radiation to reach the detector by transmission or reflection. Each detection band is centered on a wavelength of radiation that is characteristic of the absorption pattern of a specific component of the vehicle emission. Each filter on the wheel passes a detection band of radiation which corresponds to a specific vehicle emission component to be detected. The wheel and therefore the filters, rotate so that multiple vehicle emission components may be sequentially detected and analyzed using a single detector.

However, these systems have some drawbacks. For example, the use of the rotating device render a large number of parts, such as special reflectors, a variety of detectors and light filters to be manufactured, assembled, aligned, maintained, and calibrated for ensuring a proper operation of the system. Needless to say, each of these parts might introduce errors into the final measurements to some extent. For instance, the system may suffer from a light-bleed from edges of the light filters, thereby allowing undesirable wavelengths of light to be received by the detectors. Uncertainty as to the measurements may also occur because different detectors may react differently to the variety of ambient conditions encountered during the operation of these devices.

In addition, these systems can only receive a single response at each time instant, thereby a time lapse (Dt) exists between the responses for different gases components. However, such a time lapse is generally ignored in the calculation of gas components and each data point of the correlation graph for the concentration of any two of the gas components, such as hydrocarbons (HC) and carbon dioxide ($CO_2$), is assumed to be collected at the same time instant, thereby introducing significant errors thereinto. For those instable gas components such as $SO_2$, which tends to be difficult to measure with these systems of prior art due to the rapid changing character thereof, for example, $SO_2$ might easily and quickly react with water and atmospheric oxygen to form sulfuric acid during such a time lapse.

Furthermore, the use of a variety of filters, detectors, reflectors, and the like can add considerable complexity and bulk thereto. In addition, should other components of the emission be detected, the filters and/or detectors thereof also need to be replaced correspondingly, thereby involving considerable cost in parts, as well as in the assembly, alignment, and calibration thereof.

Yet another gas analysis device is disclosed in U.S. Pat. No. 4,678,914, in which a digital IR gas analyzer comprising a sample cell having a conical shaped interior wall and a filter wheel provided with HC, CO and $CO_2$ interference filters is proposed. Wherein an IR radiation from a source is directed toward an IR detector and passes through both a gas located in the sample cell and then one of various light filters mounted on the continuously rotating filter wheel. This device needs to be in close proximity to an emission output for proper operation, and it requires a sample cell for gas analysis. Such requirements are not feasible in the remote sensing of vehicle emissions, for which a sample of the emission needs to be collected and isolated from the same taken in a sample cell. Further, such a device only provides a localized reading of the gas at the exact point where the sample is taken.

There are still more systems and methods for remote sensing the exhaust emissions as disclosed in various patent publications, such as U.S. Pat. No. 5,319,199, U.S. Pat. No. 5,401,967, U.S. Pat. No. 5,591,975, U.S. Pat. No. 5,726,450, U.S. Pat. No. 5,797,682 and US 2005/0197794, each of which is in whole incorporated herein by reference.

Further, various regulations and standards on the emissions had been set forth throughout the world and all the latest automobiles on the road have to meet such stringent regulation or emissions limits thereof. The Bureau of Automotive Repair in the state of California has published a specification of On Road Emission Measurement System (OREMS) in which it lists the requirements for Remote Emission Measurement systems.

In Europe, the Euro 4 limits as specified in the Directive 70/220/EEC regulation as last amended by Directive 98/69/EC (Euro 3/4). Emission limits of Euro 3 are CO 2.3 g/km, HC 0.20 g/km, $NO_X$ 0.15 g/km and the same of the Euro 4 are CO 1.0 g/km, HC 0.10 g/km and $NO_X$ 0.8 g/km. In Japan the limits for the 10-15 mode test procedure are CO 2.1-2.7 g/km, HC 0.25-0.39 g/km $NO_X$ 0.25-0.48 g/km. The new limit introduced will drop these figures to CO 0.67 g/km, HC 0.08 g/km and $NO_X$. The limits for the USA FTP75, SC03, US 06 and highway test procedures changed from CO 3.4 g/mile, HC 0.25 g/mile & $NO_X$ 0.4 g/mile in 1994 and to CO 1.7 g/km HC 0.125 g/km $NO_X$ 0.2 g/km in 2004. In most cases the reduction is around 50% of the emission limit set forth in the past.

Other countries tend to follow or adopt these emission limits and tests procedures for vehicles locally. The new stringent emission limits of new vehicles induce increased difficulty to detect the vehicle plume. Vehicles can still become a polluter if they are not properly monitored or maintained. Having new cars in the fleet means that existing technology of the prior art would be unable to detect these vehicles as well.

In addition, exhaust emission and engine performance of a new vehicle can deteriorate after it has been in operation for a while, without the driver becoming aware of this. On Board Diagnostic (OBD) systems are widely employed in many modern vehicles to detect malfunctions of various components therein and provide a warning signal to the driver normally in the form of a warning light. However such alarms can be ignored or the warning system will fail to operate but the vehicle will still operate seeming without any change.

Modern vehicles comprise a three way catalytic converter with closed loop control. The Engine Control Unit (ECU), also known as Engine Management System (EMS) of the vehicle governs the air-fuel ratio to achieve the ideal stoichiometric ratio. For gasoline fuel, the stoichiometric air/fuel mixture is approximately 14.7 times the mass of air to fuel, i.e., 14.7 kg of air will burn ideally with 1 kg of fuel. This ratio can also be presented in terms of Lambda ($\lambda$). Fuel burning at stoichiometric mixture gives a Lambda of 1 ($\lambda=1$) at which the catalytic converter will run at its optimum efficiency. However this is not always the case in practice. In operation, the ECU will monitor air intake temperature, pressure, air flow, and numerous other sensors to achieve stoichiometric combustion. Wherein a small sensor (lambda sensor or $O_2$ sensor) inserted into the exhaust system of the engine will measure the concentration of oxygen remaining in the exhaust gas to allow the ECU to control the efficiency of the combustion process in the engine.

Whilst the vehicle engine is running under the closed loop control system the ECU will adjust automatically the quantity of fuel injected into each cylinder of engine with respect to the engine's RPM and the position of the gas pedal or throttle. To achieve stoichiometric combustion, the ECU may have to adjust the fuel intake depending on whether the engine runs rich ($\lambda<1$) or lean ($\lambda>1$). As the lambda sensor updates the ECU typically every 0.8 second whereby there is a possibility that the engine is not being run within the correct $\lambda$ value in-between each of 0.8 second interval during which the engine may have had more or less than 40 complete cycles if it runs at 3000 RPM.

There are exceptions to these rules as an ECU program may allow the vehicle to be run in open loop mode under hard acceleration (i.e. to provide extra fuel to help prevent hesitation under acceleration) which may produce higher emissions.

Currently, remote sensing systems in operation have to finish the measurement of a vehicle typically within 0.7 second due to the very short time that the emission or the plume can be measured after the vehicle has passed the system. Such remote sensing systems work well with remote sensing surveys as many cars are evaluated together to obtain a trend of the vehicle fleet emissions being measured. However, it is difficult to determine what operating status the ECU of individual vehicles being tested is currently under, i.e. the ECU can be either in transient (switching between a higher or lower stoichiometric ratio) or open loop state. As it takes time for the vehicle to restore the air-fuel mixture to the stoichiometric ratio when the mixture of air and gasoline going into the engine is rich or lean, a higher than normal exhaust emission might be accidentally sampled from the vehicle while it is passing through the remote sensing device whereby leading to an invalid or incorrect reading for the vehicle.

There are a few testing technologies being employed to test vehicle emissions. Such as stationary Idle Emission Test wherein a multi-gas analyzer, for example a four gas analyzer probe is inserted to the exhaust pipe and measures the exhaust gas with the vehicle running at idle. In the Chassis Dynamometer Test (IM240 in the USA), a vehicle is driven on a chassis dynamometer over a set of drive cycles for between 90 and 240 seconds. Dilute exhaust emission samples are extracted and measured by a complex system analyser and Constant Volume Sampling (CVS) system.

Due to the long averaging cycle of such analysers typically taking a sample rate of 1 sample per second for averaging the whole test cycle to be represented in grams per kilometer/mile whereby the change of concentration of gases CO and $NO_x$, which can indicate that a vehicle is under closed loop fuel control adjustment, would not show up under the traditional dynamometer emission testing.

In addition, none of the remote sensing systems of the prior art seems to take the transient operation of the ECU into account whereby rendering the readings taken therefrom to be inaccurate.

As for diesel smoke emission of diesel vehicle, various Diesel Smoke Emission opacity measurement standards and equipments are in use today, wherein all existing smoke tests equipments are coupled closely to the exhaust outlet of a vehicle under test. However, the use of remote sensing technique for the measurement of diesel smoke emission or particulate matter (PM) seems to be a very practical way as the vehicles have to be tested under normal driving condition. Nowadays all the remote sensing devices can make use of the TV spectrum to measure PM at the size around 200-230 nm but the majority of visible 'smoke' or PM from the diesel engine is normally represented at the size of 532 nm which is preferably sensed with green light with wavelength around 532 nm. However, there are no correlations between 530 nm and 200 nm PM produced by the combustion due to the nature of diesel engine.

Further, the remote exhaust emission sensing devices of prior art require periodical calibration during operation. The calibration will be carried out after completion of system setup and will also be required every one to two hours thereafter whereby ensuring that the readings obtained to be fallen into a specific range, if not, an adjustment can be correspondingly made for ensuring the quality thereof. Some manufacturers will carry out an initial calibration during start up process and then perform a series of calibration checks by spraying calibration gas in front of the device to see if the initial calibration has been deviated from the predetermined level with a tolerance as high as 30%. In practice such calibrations have to take place while there is enough time gap or clear space between each of the vehicles passing by such that the vehicle emissions can be dispersed substantially thereby not interfering with the calibration gas during such calibration checks. If such calibration checks and recalibration of the device cannot be successfully performed as required, the readings taken may be faulty and unusable as the overall gas readings would be severely affected by the emission from the vehicles passing by.

In fact, it is hard to perform such calibration under a variety of circumstances, especially during heavy traffic condition. In general, it will require at least 10 seconds gap between vehicles passing by. The timing of the release of calibration gas is very critical as the ambient readings will still be affected from the vehicle emissions just passed if the calibration gas was released too early. It is undesirable for using such contaminated value in the calibration process as it will eventually lead to inaccurate emission detections.

Further, the remote exhaust emission sensing systems of prior art might comprise a speed and acceleration unit for measuring the speed and acceleration of the vehicles under test, wherein a number of laser beams separately disposed from each other at a known distance. Such beams may be directed across the road and one or more reflectors can be disposed at either or both sides to reflect the light beams back to a detector at the opposite side of the road. When motor vehicle is passing by the system, the tyres will cut and interrupt the 1st beam and then the 2nd beam. The time difference therebetween or the time of interruption can be used to calculate the speed and the acceleration of the vehicle. Normally the vehicle is presumed to be a pre-specified length and contains only two axles and the front axle tyre and rear axle tyre will produce two time readings for use in the calculation of the speed and acceleration. However, some problems in obtaining the speed and acceleration readings may arise for those vehicles with 3 or more axles.

In fact, several disadvantages with these designs of prior art are known. Firstly, it is time consuming in setting up those reflectors or laser beams on either or both sides of the road as critical alignment is required and must be maintained properly on vibrating roads whereby frequent checking on the alignment thereof is necessary, especially in days with high winds. In addition, the use and deployment of such extra equipments on the road can potentially become a safety hazard to the road users. Further, low profile tyres, motor cycles, trucks with three or more axles and objects hanging down from the vehicles will interfere and produce false triggers to such equipments with old designs whereby leading to a miss or an abnormal number in the speed and acceleration reading. As such equipments sometimes cannot correctly determine the rear end of the vehicle for at least the above reasons, a license plate picture of the vehicle passing by is thus cannot be successfully obtained by corresponding associated equipments whereby rendering the performance of the whole system to be adversely affected. Further, as the wheel base distance is estimated and used in the calculation of the speed and acceleration but an estimation of a fixed wheel base length of passing vehicle will incur errors in the results of the calculation.

Further, remote sensing systems of the prior art are normally powered by mains electricity or have the electrical power being supplied from a gasoline or diesel engine generator when working in the field. In general, such generators have a less sophisticated emission control system than that of the vehicles being under test and are very noisy and heavy thereby they have to be placed at a distance from the test site. This also prevents engine emission and engine noise reaching the test site but such engine emission in fact can eventually pollute the test site due to localized climatical changes in wind directions. The exhaust emissions expelled from the engine generator into the background are thus undesirable in measuring emissions of vehicles passing through the system. In addition, such a power supply system also requires long and heavy power cables to reach the remote sensing test site. Some remote sensing systems have such a generator built into a custom made van, which is very expensive and requires extensive modifications to the van. The parking location of the van will be also restricted as it is not always possible to be parked nearby the testing location of the remote sensing equipment.

Also, some remote sensing systems of the prior art are being controlled by a PC, which is connected to the remote sensing device by a series of long and heavy cables. Motorists seeing such cables' or abnormal devices with wires running from boxes leading to a van or table of equipment would tend to change their driving pattern slightly while they were traveling the road under test conditions. This can be due to their curiosity to observe the event or out of fear that it may be a speed trap or other enforcement device.

SUMMARY OF THE INVENTION

It is therefore an object of the present invention to overcome at least partially the foregoing drawbacks in the prior art, and more particularly, to provide an effective remote vehicle emissions measurement system to detect at least multiple gas components in a concurrent and instantaneous manner without the use of rotating devices, such as rotating mirrors, movable rotating filters or the like.

Another object of the present invention is to enhance the accuracy and certainty of the remote vehicle emissions measurement system by reducing the number of parts and eliminating the need of rotating devices thereof.

A further object of the present invention is to allow the multiple responses for various gas components to be received and processed concurrently at any one time instant such that the accuracy thereof can be improved over the same of the prior art.

Yet another object of the present invention is to allow periodic self calibrations or auto audit of an remote vehicle emissions measurement system to be performed without the interference from the ambient gas or exhaust emission of the vehicles under test whereby ensuring the measurement accuracy thereof.

Yet still another object of the present invention is to further detect smoke emission or particulate matter at the size not only around 200 nm-230 nm but also around 532 nm for diesel engine.

Yet still another object of the present invention is to further enhance the accuracy level of each reading taken by eliminating the unwanted erroneous data obtained in transient mode of the vehicle under test with one or more remote vehicle emissions measurement system according to the present invention.

One aspect of the present invention provides a compact remote vehicle emissions measurement system comprising a radiation source for emitting a light beam of a set of predetermined wavelength bands through an emission plume of a vehicle; an adaptable radiation detection unit for receiving the set of predetermined wavelength bands passing through the emission plume; an optional image capture unit for capturing or recording an image of the vehicle passing through the measurement system; an optional speed and acceleration detection unit for detecting the speed and acceleration of the vehicle passing through the measurement system; and a processing unit respectively interconnects with the speed and acceleration detection unit, the image capture unit and the radiation detection unit for analyzing and processing the data collected by the speed and acceleration detection unit, image capture unit and radiation detection unit; wherein the radiation source comprises an infrared source, an ultraviolet source or a combination thereof; the adaptable radiation detection unit comprises one or more detachable and expandable detecting elements for receiving the set of predetermined wavelength bands and producing a plurality of corresponding response concurrently at any one time instant as required; and the processing unit comprises one or more specific software and hardware for calculating the concentrations of various gas components thereof, the relative ratio of one gas component to the others, or the absolute emission values of each of the gas components thereof.

Preferably, the foregoing system further comprises an embedded power supply unit for elimination of unwanted background pollutants as produced by external gasoline or diesel generators and the deployment of long and heavy power cables thereof.

Preferably, the foregoing system further comprises an embedded wireless communication unit for allowing the system to be conveniently controlled by means of wireless network communication, thus serving as a telemeter that transmits measurement data to a controlling device disposed at a distance.

Alternatively, the foregoing system further comprises at least two microwave or ultrasonic transceiver for the measurement of speed and acceleration of the vehicles under test and the discrimination of the rear end of vehicles such that a proper picture of which can be taken for further processing.

Alternatively, the foregoing system further comprises a green light or green laser source with its wavelength ranging from 515 nm to 540 nm to detect diesel smoke emission or particulate matter at the size around 532 nm.

Preferably, the foregoing system further comprises a small calibration gas chamber disposed within the radiation path and the chamber can always be filled and refilled with new charge of calibration gas for each calibration conducted as required.

Alternatively, the foregoing system further comprises one or more reflectors mounted in a manner to allow the radiation from the source to be directed to the radiation detection unit and the one or more detecting elements thereof.

Preferably, each of the one or more detachable and expandable detecting elements can further comprises one or more alternative photodetectors enclosed therein in a compact manner, wherein a band pass filter is provided before each of them for respective wavelength band detection, and thereby forming an array of photodetectors for producing concurrently a plurality of response thereto.

Alternatively, the adaptable radiation detection unit can comprise a spectrometer or a photomultiplier tube or the like for producing concurrently a plurality of response.

Thus, the present invention can measure concurrently many more species of gas at any one time instant, including those instable species such as $SO_2$ in the UV spectrum, from 205 nm to 215 nm and from 280 nm to 290 nm.

The other aspect of the present invention provides a method for remote sensing the emissions of a vehicle independent of the transient operation of the ECU, comprising the steps of gathering a predetermined number of data points relative to an emission plume of the vehicle with one or more remote vehicle emissions measurement system, such as the foregoing one. The method further comprises the steps of checking whether there is any transient change between CO and $NO_X$ to determine if the vehicle is in transient mode for the elimination of unwanted erroneous data points; and calculating and presenting the concentrations of various gas components thereof, the relative ratio of one gas component to the others, or the absolute emission values of each of the gas components thereof with remaining data points. Wherein the predetermined number of data points might range from 5-100, and shall be normally set at 6-30 while the preferred value is around 20-30.

The remote vehicle emissions measurement system of the present invention can be located at roadside for measuring the exhaust emissions directly from a vehicle passing by. There is no need for a cell or chamber in which to gather the emission plume for measuring the concentrations of various gas components thereof. Further, the configuration of the present invention allows the respective emissions of each of the passing by vehicles to be measured instantaneously over a short time span, thereby providing the concentrations thereof in an accurate and practicable manner.

Other features and advantages of the present invention will be apparent to those skill in the art from the detailed description of the preferred embodiments of the below with reference to the drawings.

BRIEF DESCRIPTION OF THE DRAWINGS

FIGS. 5a-5c illustrate schematic views of a calibration gas chamber of an embodiment of the present invention.

DETAILED DESCRIPTION OF THE INVENTION

Figure 1:
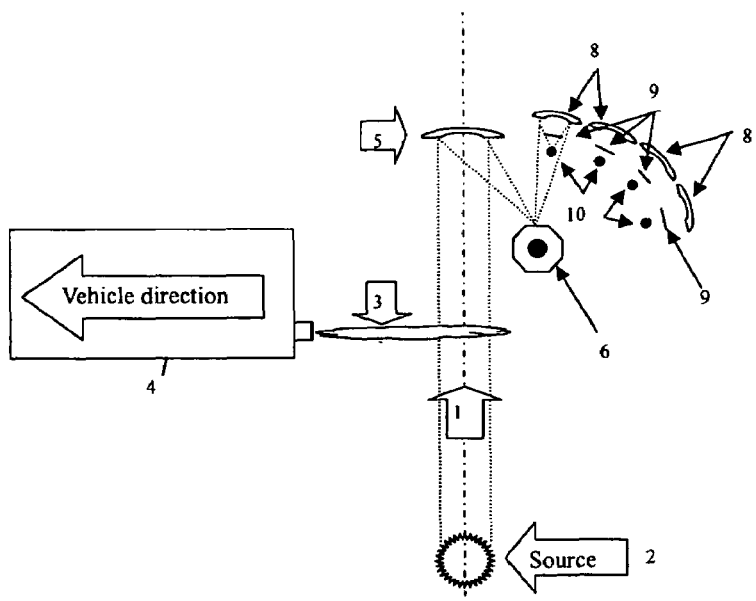
FIG. 1 illustrates a prior art remote vehicle emissions measuring device.

FIG. 1 illustrates a prior art remote vehicle emissions measuring device, wherein a beam 1 emitted from a radiation source 2 passes through the emissions plume 3 of vehicle 4 and is reflected from a mirror 5 onto a reflecting wheel 6. The beam 1 is in turn reflected from the reflecting wheel 7 to one of a group of mirrors 8; thereby it is then focused and reflected onto the respective detectors 10 through respective filters 9 thereof.

Figure 2:
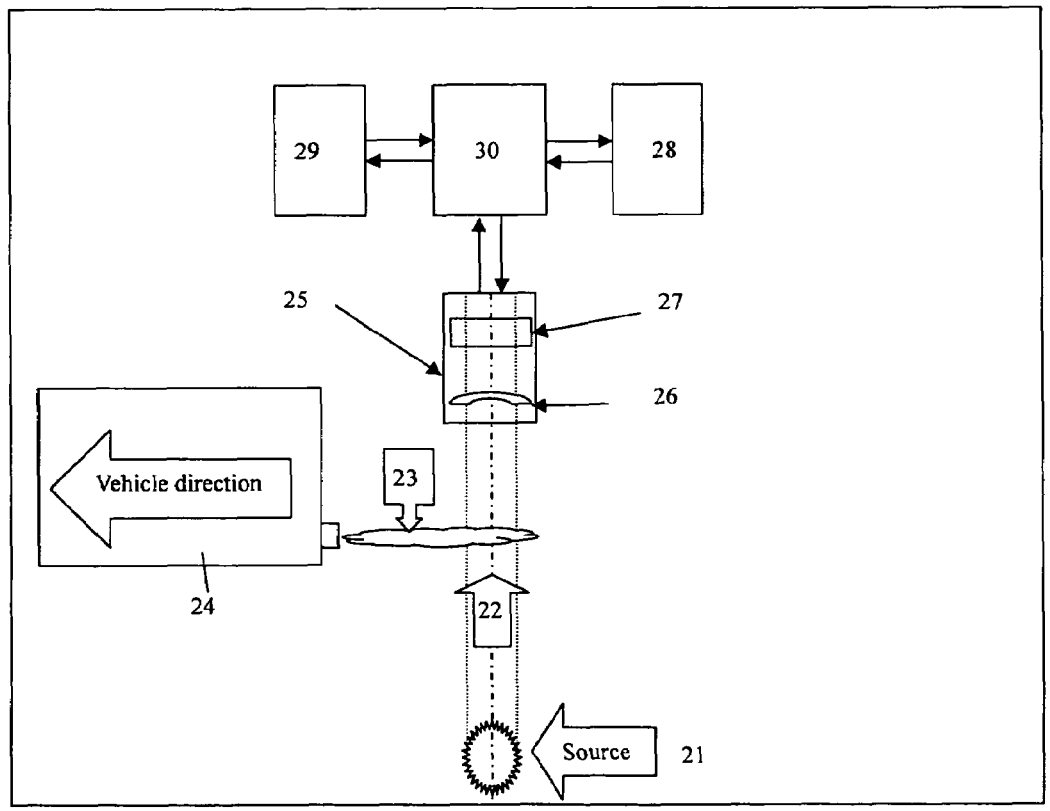
FIG. 2 illustrates an embodiment of a remote vehicle emissions measurement system in accordance with the present invention.

Referring to FIG. 2, an embodiment of a remote vehicle emissions measurement system in accordance with the present invention is illustrated, which can be used to remotely determine components of vehicle emissions and provided at a number of different locations, such as an entrance or exit ramp of a highway or the like. It may be moved to a different location and employed at the new location to sense the same or different components of vehicle emissions as required. It may also be used as a permanent fixing at the roadside, and the data collected as well as the results thereof may be sent to a head office or stored for future analysis.

The embodiment comprises a radiation source 21 for emitting a light beam 22 of a set of predetermined wavelength bands through an emission plume 23 of a vehicle 24. It further comprises an adaptable radiation detection unit 25 for receiving the set of predetermined wavelength bands passing through the emission plume 23, wherein the beam 22 can be alternatively converged and intensified by means of a lens 26 before reaching one or more detachable and expandable detecting elements 27 arranged therein; an optional image capture unit 28 for capturing or recording an image of the vehicle 24; an optional speed and acceleration detection unit 29 for detecting the speed and acceleration of the vehicle 24; and a processing unit 30 respectively interconnects with the speed and acceleration detection unit 29, the image capture unit 28 and the radiation detection unit 25 for analyzing and processing the data collected respectively by the units 25, 28, 29.

Alternatively, the processing unit 30 can be interconnected with an embedded power supply unit (not shown) and/or an embedded wireless communication unit (not shown), respectively.

The radiation source 21 emits electromagnetic radiation for use in the absorption spectroscopy measurement of vehicle exhaust emissions. Preferably, the source 21 may comprises those readily available in the market, such as an infrared (IR), near infrared (NIR) or mid Infrared (MIR) radiation source that are possibly utilizing a Tungsten/Halogen lamp with wavelengths ranging from 220 nm to 2500 mm, a Nichrome wire with wavelengths ranging from 750 nm to 20,000 nm, a Globar with wavelengths ranging from 1200 nm to 60,000 nm, or a Nernst Glower with wavelengths ranging from 400 nm to 20,000 nm, in the generation of the beam 22. Alternatively, other types of radiation sources can be used as well, for example, an ultraviolet (UV) source which is possibly utilizing a Xenon Lamp with wavelengths ranging from 250 nm to 600 nm, a H2 and D2 Lamps with wavelengths ranging from 160 nm to 380 nm, or a combination thereof to generate the beam 22. While any other similar sources in the market that are not listed above may also be alternatively used in an embodiment of the present invention such that a light beam 22 of a set of predetermined wavelength bands can be generated and emitted through an emission plume 23 of a vehicle 24.

In order to measure not only the gasoline but also the diesel smoke emission or particulate matter in a more accurate manner, the radiation source can alternatively comprises a green light or green laser source with its wavelength ranging from 515 nm to 540 nm in view of the particulate matter size of a diesel engine vehicle. Preferably, a $CO_2$ channel can be incorporated such that the ratio of particulate matter to $CO_2$ can be used to calculate and correlate the traditional industrial smoke number or the percentage of opacity. Wherein the smoke number is one of the measurements for the smoke (carbon-particulate emission, particulates), which is indicated as % opacity or alternatively be presented as k coefficient of light absorption "m−1", Hartridge Smoke Units "HSU", Filter Smoke Number "FSN" and mg/m3. According to the present invention, the particulate matter can be also measured within the visible light range. This enables the measurement of particulate matter at various different wavelengths whereby the quantities of particulate matter at different sizes can be correspondingly determined.

Figure 3A:
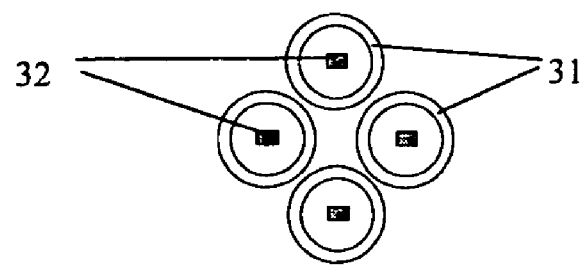
FIGS. 3a-3c illustrate schematic views of the parts of embodiments of a remote vehicle emissions measurement system in accordance with the present invention.
Figure 3B:
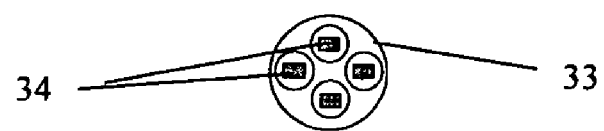

The one or more detachable and expandable detecting elements of the adaptable radiation detection unit 25 can be configured in different manners, as shown in FIGS. 3a-3b, for receiving the set of predetermined wavelength bands passed through the emission plume 23 and producing a plurality of corresponding response concurrently at any one time instant as required. Preferably, each of the one or more detachable and expandable detecting elements 31 can further comprises one or more alternative photodetectors 32, such as photodiodes, enclosed therein in a compact manner, wherein a band pass filter can be provided before each of the photodetectors 32 for respective predetermined wavelength band detection, and thereby forming an array of detecting elements 31 for producing concurrently a plurality of response thereto and no rotating device, such as a reflecting mirror wheel or a movable filter wheel, is required by present invention. Further, while each of the detecting elements 31 can enclose a photodetector 32 therein, a plurality of photodetectors 34 can also be enclosed in the same detecting element 33 in a close packing manner as shown in FIG. 3b.

Figure 3C:
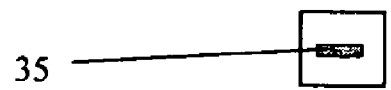

Alternatively, the adaptable radiation detection unit 25 can comprise a spectrometer 35, a photomultiplier tube or the like for producing concurrently a plurality of response as shown in FIG. 3c. For an embodiment using ambient radiation sources, an appropriately sensitive detector may be used. For example, a lead selenide (PbSe), a mercury cadmium telluride (Hg Cd Te) photodetector (cooled or non-cooled), or linear array of foregoing photodetectors or the like may be used to detect the ambient IR or UV radiation therein.

Further, one or more reflectors can be incorporated thereinto, which can be mounted in a manner to allow the radiation from the source to be directed to the adaptable radiation detection unit 25 and the one or more detecting elements 27 thereof. The reflector may comprise a mirror, prism, diffraction grating, beam splitter or the like. The reflectors may be integrated with the radiation detection unit 25. In this case, each of the reflectors may function to split the radiation beam among the one or more detecting elements 27, to focus the radiation beam onto the one or more detecting elements 27 and/or to redirect the radiation beam to other additional detecting elements for detection of a specific gas component.

The reflector may also comprise a lateral transfer mirror for reflecting the beam 22 back along a path displaced laterally (or vertically) from the path between the source 21 and the reflector. In this case, the reflector will be generally located separately from the radiation detection unit. The primary purpose of such a transfer mirror is to redirect the beam 22 to the radiation detection unit 25. A variety of different transfer mirrors may be employed depending on the spatial relationship of the radiation source 21, radiation detection unit 25 and the reflector thereof.

The image capture unit 28 may comprise a camera, a digital camera or camcorder or the like for capturing or recording an image of the vehicle passing through the measurement system.

Preferably, the image capture unit 28 may record an image of the vehicle license plate or tag, which can be further processed with a suitable data processor to gather some additional relevant information thereof. For example, local Motor Vehicle Department databases may be accessed to retrieve the make, model type and model year of the vehicle 24 such that the condition and the existence of any specific device or mechanism for use in the engine of the vehicle 24, such as a carburettor, fuel injector, catalytic converter or the like can be taken into account during the further analysis and/or calculation conducted by the processing unit 30 thereof.

The speed and acceleration detection unit 29 may comprise an arrangement of laser emitters together with a timing circuitry for arranging multiple laser beams traversing the path of the vehicle 24 at various points in the system. While the vehicle 24 passes through the system, interruptions in the laser beams will be caused and the times or durations at which the beam interrupts occur may be used to calculate the vehicle's speed and acceleration. Other methods of detecting vehicle speed and acceleration may also be used. For example, radar systems, transducers or piezoelectric elements, speed and acceleration detection camera or the like may be placed at various locations in the roadway to monitor the path thereof.

According to the present invention, the speed and acceleration detection unit 29 may alternatively comprise two microwave or ultrasonic transceivers for respectively transmission of a signal to the drive lane from the roadside and reception of the signal reflected from a vehicle running on the lane, wherein each signal creates a trace which can be overlaid onto the other trace and the peaks of these two traces can be analyzed to determine the changes in speed and acceleration obtained while the vehicle was passing by the system. The advantages of the present invention over the prior art will be apparent to a person skilled in the art as no time consuming and complicated setup required and the adverse effect of low profile tyres, motor cycles, trucks with three or more axles and objects hanging down from the vehicles as well as the error caused by the estimation of a fixed wheel base length will be eliminated as they will be detected as a whole as one single object by this approach whereby the rear end and thus the license plate picture of the vehicle can be faultlessly determined and obtained. Further, as the speed and acceleration unit 29 of the present invention can eliminate the interference from other vehicles to a vehicle under test in a multilane environment, it enables the remote emission measurements for vehicles or traffic on a multilane road by the deployment of two speed and acceleration detection unit 29 respectively on each side of the road.

Preferably, the speed and acceleration data may be further processed by the processing unit 30 to accurately characterize vehicle operation conditions, such as accelerating or decelerating. Other uses of the speed and acceleration data are also possible. For example, for use in a traffic speed survey at various site locations to help determine whether the speed limits thereof need to be revised for specific roads or areas; for vehicle speed enforcement purposes at different locations by the police; for research purposes to help manufacturers of vehicles determine a specific speed and or acceleration rate at which a vehicle may be producing a very higher emission profile, due to the vehicle emission control going into open loop mode under acceleration and/or the determination of the best optimized vehicle speed to the most optimized emission output of traffic on any specific road or area.

The processing unit may comprise one or more specific software and hardware, such as a PC with TCP/IP network connections or the like on which one or more software is running, for analyzing and processing the data collected by the radiation detection unit 25, image capture unit 28, speed and acceleration detection unit 29, thereby calculating the concentrations of various gas components thereof, the relative ratio of one gas component to the others, or the absolute emission values of each of the gas components thereof. For example, the software may be used to calculate the concentrations of various exhaust gas components such as HC, $CO_2$, $NO_X$, CO, etc.; the decay rate such as the dissipation in time of the exhaust components; the opacity of the exhaust plume 23, the temperature of the vehicle and the like. Alternatively, software may be used to calculate detected ratios between $CO_2$ and other exhaust components. Further, the software may also be used to calculate absolute emission values. This may be achieved by reading absolute values worked back from the plume size after the vehicle 24 has passed by the system, taking each gas component reading as the same of an individual gas.

The software may further make comparisons to threshold concentration values or emission profiles for characterization of vehicles 24 as high or low emitting vehicles and to ensure the compliance with such predetermined emission standards.

The processing unit 30 may further comprise software routines to accomplish other data analysis functions. For example, the vehicle emission data may be checked for running losses, which may typically include emission readings due to fuel system leaks on a vehicle, such as leaky fuel tank filler cap, fuel line, leaking evaporative charcoal canisters, etc.; blow by emissions such as emissions due to other vehicles in the vicinity; or other systematic losses thereof.

The processing unit 30 may also include software routines to accomplish various vehicle owner notification processes. For example, a vehicle owner of a vehicle that has been recorded as "clean", namely in compliance with certain predetermined emission levels, may receive notification upon a second recording of "clean". In this case, coordination with local authorities may be arranged to grant the vehicle owners a waiver or pass of local emission certification procedures upon receiving such a clean notification. Likewise, owners of vehicles that fail to meet predetermined emission levels may receive notification requiring the owner to remedy the non-compliance. Other data processing functions are also possible.

The remote vehicle emissions measurement system of the present invention is able to meet and exceed the requirements set forth by various countries. As the instantaneous readings of all the gases eliminate errors in readings that other machines in the prior art inherently have. Such errors are caused by assumptions being made that all gases are read at the same time due to detector methodology thereof, (i.e. spinning mirrors and filter methods having as much as 20 ms delay between each gas component detection). The plume will decay over time and such a delay caused by the moving devices during each gas reading will result in a change of the concentration thereof. The system of present invention will only be limited by the sampling speed of the detecting elements of the detection unit, which can run as quick as 0.05 ms. Such high speed or resolution of the present invention ensures an accurate reading and improved capture rate of vehicles passing through the beam at any speed, more particularly the vehicles moves in higher speed which the prior art devices struggle to capture.

Thus, the present invention can measure concurrently many more species of gas within a very short duration so that those instable species such as $SO_2$ can be detected properly before it dissipates into the air.

Further, having more than one gas ($H_2O$, $SO_2$, CO, $CO_2$, $NO_X$, $NH_3$, HC) to be detected in a concurrent manner rendering the readings obtained therefrom can be further used to eliminate the effect of the ambient humidity and the presence of the other gases in the path, thereby allowing the present invention to be used in all weather. Similarly, this will also help reduce the interference from spectral signal overlapping wavelengths.

Alternatively, the remote vehicle emissions measurement system of the present invention can be powered by the embedded power supply unit, which includes a storage battery, such as a 5V, 12V or 24V battery for the elimination of the unwanted background pollutants as produced by previously mentioned conventional gasoline or diesel generators. The employment of multiples of batteries can ensure continuous power supply as each individual battery can be replaced to guarantee a continuous flow of clean and stable power during operation. Further, alarms in the software can automatically shut the PC and remote sensor system down whenever necessary, such as low in power or low in space, as opposed to generators stalling and a sudden loss of power which can possibly corrupt the PC's hard disk. Using a battery operated system requires no long and heavy power cables and will make setup easier and the choice of location less restrictive. It will run safer and quieter, and is less noticeable by the driver passing by, who in turns will drive "normally".

Alternatively, the remote vehicle emissions measurement system of the present invention can be controlled, by means of the wireless communication unit incorporated into the processing unit or embedded as a standalone unit that employs wireless network communication protocols such as WiFi, WiMAX or bluetooth or the like, under wireless control from a lap-top computer or pocket PC or other PC restricted only by the interface. Further, such wireless communication unit may make use of other wireless communication protocols if necessary, for example, GPRS, and those 3G or even 4G protocols such as UMTS, FOMA, WCDMA, CDMA-2000, TD-SCDMA and the like. This reduces the amount of long and heavy cables which are required for other systems to communicate from PC to remote sensor 32. Having such wireless communication unit incorporated into the system enabling the monitoring and controlling of more than one remote sensor unit at any given time. This also reduces setup time as there is no long and heavy cables to untangle, thus providing more choices of test sites which could not otherwise be chosen with existing remote sensing devices of the prior art.

Accordingly, a compact remote vehicle emissions measurement system according to this embodiment of the present invention having several advantages over the same of the prior art. Firstly, it enables the controlling and monitoring of many unmanned remote sensing devices around a district could be performed by a central processing office whereby reducing the labour costs thereof. Secondly, it enables the controlling and monitoring of remote sensors from a covert on site locations without wires leading from the remote sensor to the operator station as it is smaller in size and thus being much easier to be concealed on or within a common road side equipment such as a traffic cone. Therefore, the whole system can be covert and less obstructive to road users and pedestrians alike whereby it can be disposed freely and does not need to be restricted to any specific lane. Further, it requires no noisy generators which might produce background emission whereby there is no noise and pollution problems. Further, the deployment of the whole system is also much easier as no long and heavy cables to contend with whereby it is safer for the operator during the road side setup procedures of the system as it requests less time in carrying out the installation work at the road side.

In order to further enhance the accuracy level of each reading taken, the present invention provides a method for remote sensing exhaust emissions without being affected by the transient operation of the ECU. It comprise a step of gathering a predetermined number of data points relative to an emission plume of the vehicle with one or more remote vehicle emissions measurement system, such as the one according to this embodiment. The method further comprises the steps of checking whether there is any transient change between CO and $NO_X$ to determine if the vehicle is in transient mode for the elimination of unwanted erroneous data points; and calculating and presenting the concentrations of various gas components thereof, the relative ratio of one gas component to the others, or the absolute emission values of each of the gas components thereof with remaining data points. Wherein the predetermined number of data points ranges from 5-100, and 6-30 may be a better choice while the preferred value is around 20-30.

The data points collected can be used for determination of data trend to identify whether a vehicle's ECU is in normal state or in transient mode, i.e. it is switching between a high or low air fuel ratio or in open loop. The use of more than one systems according to this embodiment will further help identifying and ruling out erroneous high readings that are occasionally emitted from clean vehicles and the additional system can also act as a back up for determining if a vehicle is logged as a dirty emitting vehicle. Further, such erroneous high readings will probably be either considered as an error or collected and averaged.

Figure 4A:
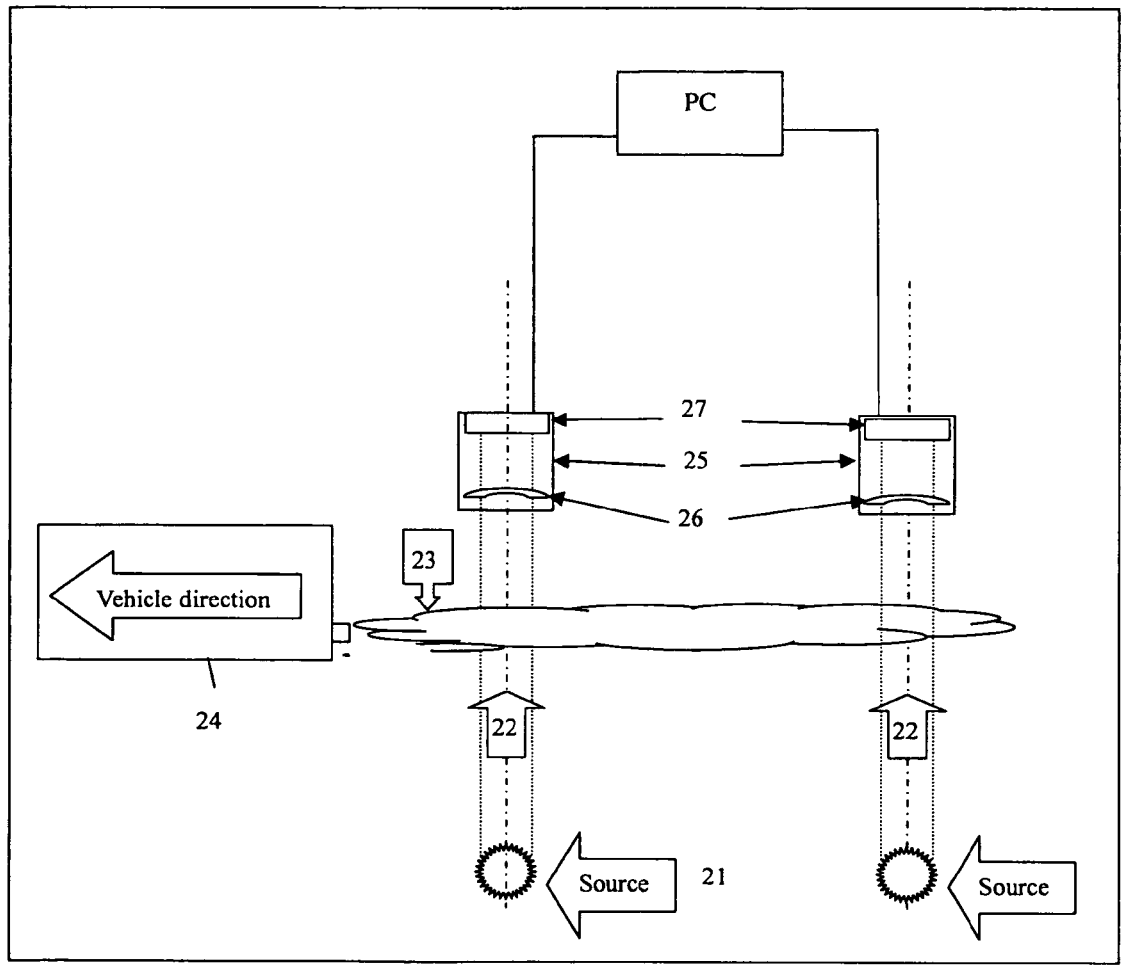
FIGS. 4a-4b illustrate schematic views of an embodiment of the present invention, in which two remote vehicle emissions measurement system has been employed.
Figure 4B:
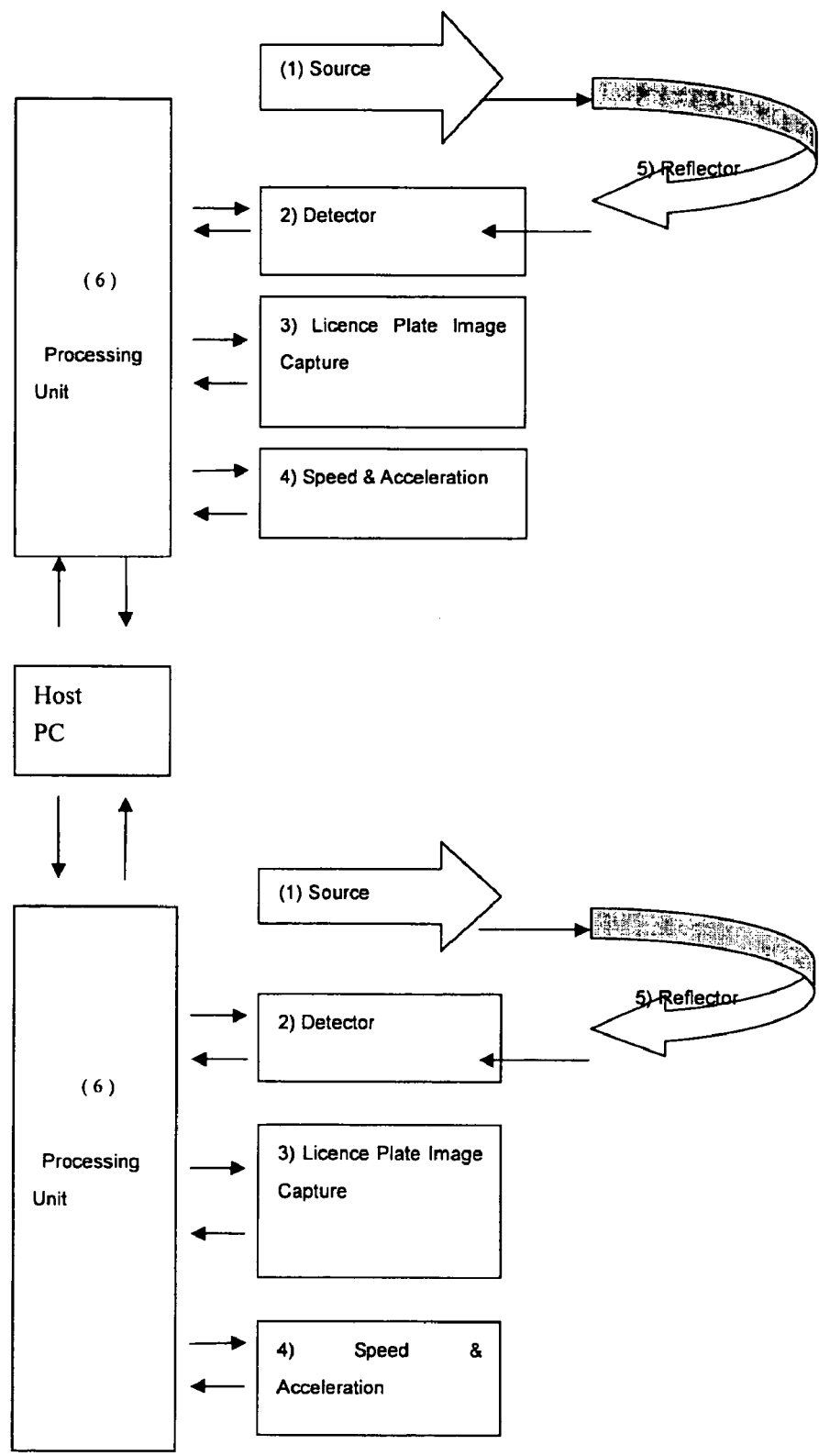

According to the present invention, carbon monoxide (CO) and nitrogen oxide ($NO_X$) in exhaust emission are opposites of each other by nature, i.e. if $NO_X$ is high then CO would be low and vice-versa. If the vehicle were in transient mode then the readings of such two gases would change in opposite direction as the ECU is trying to correct the fuel and air mixture to maximize the efficiency of the engine. Therefore, if there is any trend of changes on the CO, $NO_X$ and $CO_2$ channel, the relevant data can be ignored so as to eliminate the effect of the transient switching of the ECU. The purpose of this calculation procedure is to enhance the accuracy level of each reading taken such that the readings can be adapted for enforcement purposes. As the elimination of the transient points contained within the data trend will definitely provide a reading corresponding to the actual vehicle condition in a more accurate manner whereby the measurement result will be relatively true and seemed to be more enforceable. Consequently, the measuring systems according to the present invention may be used for enforcement purposes as required, wherein it can further comprises some enforcement parameters and acceptable tolerances that can be correspondingly determined by the enforcement authorities. FIGS. 4a-4b illustrate an embodiment of the present invention in which two remote vehicle emissions measurement system has been employed for further enhancement of the accuracy thereof. In general, the employment of just one of such system will be adequate in view of the flexibility of the system according to the present invention, wherein the software and hardware can be adaptively and easily changed and adjusted for detection of any specific gas components in the exhaust emission of a vehicle in a fast and accurate manner.

FIGS. 5a-5c illustrate another embodiment of the present invention, which comprises a small calibration gas chamber 50 disposed within the radiation path for carrying out self calibration as required. The chamber comprises a front 51 and a rear window 52 made of transparent material by which the radiation can be passed through, a gas inlet 53 with a first solenoid valve being connected to a gas supply 54 for injecting the calibration gas thereinto, a gas outlet 55 with a second solenoid valve being connected to an air pump 56 for extracting the calibration gas therefrom. Preferably, it further comprises a pressure sustaining valve 57 for maintaining the internal pressure of the chamber at a specific level.

In operation, the first solenoid valve opens and the calibration gas is fed from the gas supply and injected into the chamber. After the completion of the calibration, the first solenoid valve closes while the second solenoid valve opens, and then the calibration gas will be extracted out of the chamber by the air pump.

As the $NO_X$ gas in the chamber will be decayed by UV light after being exposed to it for a length of time and such a change is noticeable in 10 minutes, the chamber will be always filled and refilled with a new charge of calibration gas within a predetermined time frame such as 2 minutes for allowing the calibration to be conducted in a faultless way.

The configuration of this embodiment will also be able to perform auto audit even as required in heavy traffic. Several governments or authorities require an audit of calibration to be performed during the test for ensuring the accuracy of the system. However, it is difficult for systems of prior art to do a self calibration with reference to a sample calibration gas which will probably and easily be polluted by the ambient gas or the exhaust emissions from the traffic. According to this embodiment, the system will initially monitor and record the ambient gas value as a reference value. In operation, once a vehicle passes through the system and the ambient gas was found to be diluted to the reference value, the system will trigger a gas release for the audit check.

The refillable calibration gas chamber of present invention make use of a fresh and clean calibration gas, which has not been exposed to and degraded by UV light, to conduct the calibration whereby each calibration will remain accurate.

As the gas contained inside the chamber will be deteriorated by UV radiation, it will be extracted to the atmosphere by the air pump after each calibration and then a new charge of calibration gas will be injected into the chamber from the gas supply right before the next calibration. As such, the gases in the chamber will be undiluted and under a condition of stable pressure and temperature relative to the ambient condition.

Preferably, the calibration gas chamber can further comprise a gas concentration regulator for regulating the concentration of the calibration gas contained therein. For example, the calibration gas chamber might comprise one or more movable side walls capable of back and forth movement whereby changing the volume of the chamber and thus the concentration of the gas therein and such movable side walls can be acted as the gas concentration regulator therefor. Alternatively, the pressure sustaining valve can be replaced by an adjustable pressure regulator to vary the pressure therein while keeping the volume of the chamber unchanged. Similarly, an adjustable temperature regulator might alternatively be employed as the gas concentration regulator whereby changing the internal temperature of the chamber and thus the concentration of the gas therein. Such configurations of the chamber according to the present invention enabling the calibration to be conducted under various pressure and the multiple data points or readings obtained therefrom gives the ability to confirm the linearity of the readings throughout the span of emission reading ranges.

It should be understood that the present invention is not limited to above embodiments, and many corresponding modifications as well as variations are also possible and can be made by one skilled in the art as according to the teachings of the present invention, while such modifications and variations fall into the scope of the claims of the present invention.

What is claimed is:

1. A remote vehicle emissions measurement system comprising:
    a radiation source for emitting a light beam of a set of predetermined wavelength bands through an emission plume of a vehicle;
    an adaptable radiation detection unit comprising a plurality of detachable and expandable detecting elements, the plurality of detecting elements adapted to simultaneously receive the set of predetermined wavelength bands passing through the emission plume and produce a plurality of corresponding responses concurrently at any one time instant as required, the plurality of detachable and expandable detecting elements being grouped together in a compact manner;
    a processing unit interconnects with the radiation detection unit for analyzing and processing the data collected by the radiation detection unit, the processing unit comprising one or more specific software and hardware for calculating the concentrations of various gas components thereof, the relative ratio of one gas component to the others, or the absolute emission values of each of the gas components thereof; and
    means for checking whether there is any transient change between CO and $NO_x$ to determine if the vehicle is in transient mode for the elimination of unwanted erroneous data points.

2. The system as claimed in claim 1, wherein it further comprises an embedded power supply unit.

3. The system as claimed in claim 1, wherein it further comprises an embedded wireless communication unit employing a wireless network communication.

4. The system as claimed in claim 1, wherein it further comprises a small calibration gas chamber disposed within the radiation path wherein the calibration gas chamber comprises a front and a rear window made of transparent material by which the radiation can be passed through, a gas inlet with a first solenoid valve connected to a gas supply, a gas outlet with a second solenoid valve connected to an air pump.

5. The system as claimed in claim 4, wherein the calibration gas chamber further comprises a pressure sustaining valve for maintaining the pressure therein.

6. The system as claimed in claim 4, wherein the calibration gas chamber further comprises a gas concentration regulator for regulating the concentration of the gas contained therein.

7. The system as claimed in claim 6, wherein the calibration gas chamber comprises one or more side walls capable of back and forth movement whereby forming the gas concentration regulator.

8. The system as claimed in claim 6, wherein the gas concentration regulator comprises an adjustable pressure regulator or a temperature regulator.

9. The system as claimed in claim 1, wherein it further comprises one or more reflectors mounted in a manner to allow the radiation from the source to be directed to the plurality of detecting elements thereof.

10. The system as claimed in claim 1, wherein each of the plurality of detachable and expandable detecting elements further comprises one or more alternative photodetectors enclosed therein in a compact manner for respective wavelength band detection, thereby forming an array of photodetectors for producing concurrently a plurality of responses thereto.

11. The system as claimed in claim 10, wherein a band pass filter is provided before each of the one or more alternative photodetectors for respective wavelength band detection.

12. The system as claimed in claim 1, wherein the radiation detection unit alternatively comprises a spectrometer or a photomultiplier tube.

13. The system as claimed in claim 1, wherein it further comprises an image capture unit being interconnected with the processing unit for capturing or recording an image of the vehicle.

14. The system as claimed in claim 1, wherein it further comprises a speed and acceleration detection unit being interconnected with the processing unit for detecting the speed and acceleration of the vehicle.

15. The system as claimed in claim 14, wherein the speed and acceleration detection unit alternatively comprises at least two microwave or ultrasonic transceiver.

16. The system as claimed in claim 1, wherein the radiation source comprises a green light or green laser source with its wavelength ranging from 515 nm to 540 nm for the measurement of smoke emission and particulate matter of a diesel engine vehicle.

17. A method of remote sensing the emissions of a vehicle without being affected by the transient operation of the ECU, comprising the steps of:
    gathering a predetermined number of data points relative to an emission plume of the vehicle with one or more remote vehicle emissions measurement system;
    checking whether there is any transient change between CO and $NO_x$ to determine if the vehicle is in transient mode for the elimination of unwanted erroneous data points; and calculating and presenting the concentrations of various gas components thereof, the relative ratio of one gas component to the others, or the absolute emission values of each of the gas components thereof.

18. The method as claimed in claim 17, wherein the redetermined number of data points ranges from 5-100.

19. The method as claimed in claim 17, wherein the redetermined number of data points ranges from 20-30.

* * * * *